United States Patent
Avitsian et al.

(10) Patent No.: US 9,763,562 B2
(45) Date of Patent: Sep. 19, 2017

(54) MEDICAL DEVICE SHEATH

(71) Applicant: THE CLEVELAND CLINIC FOUNDATION, Cleveland, OH (US)

(72) Inventors: Rafi Avitsian, Solon, OH (US); Andrew Zura, Cleveland, OH (US); Ji-Feng Chen, Lakewood, OH (US)

(73) Assignee: The Cleveland Clinic Foundation, Cleveland, OH (US)

(*) Notice: Subject to any disclaimer, the term of this patent is extended or adjusted under 35 U.S.C. 154(b) by 78 days.

(21) Appl. No.: 14/506,945

(22) Filed: Oct. 6, 2014

(65) Prior Publication Data

US 2015/0031955 A1 Jan. 29, 2015

Related U.S. Application Data

(63) Continuation of application No. 13/257,529, filed on Mar. 7, 2012, now Pat. No. 8,870,752.

(51) Int. Cl.
| | | |
|---|---|---|
| *A61B 1/04* | (2006.01) | |
| *A61B 1/00* | (2006.01) | |
| *A61B 1/012* | (2006.01) | |

(52) U.S. Cl.
CPC ...... *A61B 1/00135* (2013.01); *A61B 1/00078* (2013.01); *A61B 1/00142* (2013.01); *A61B 1/012* (2013.01)

(58) Field of Classification Search
CPC ............ A61B 1/00135; A61B 1/00142; A61B 1/00078; A61B 1/012
USPC ............... 600/114, 117, 121–125, 127, 129
See application file for complete search history.

(56) References Cited

U.S. PATENT DOCUMENTS

| | | | |
|---|---|---|---|
| 4,646,722 A | | 3/1987 | Silverstein et al. |
| 4,741,326 A | | 5/1988 | Sidall et al. |
| 5,025,778 A | * | 6/1991 | Silverstein ........... A61B 1/0008 600/104 |
| 5,201,908 A | | 4/1993 | Jones |
| 5,503,616 A | * | 4/1996 | Jones ................. A61B 1/00135 600/121 |
| 5,749,889 A | * | 5/1998 | Bacich ............... A61B 17/3417 600/104 |

(Continued)

FOREIGN PATENT DOCUMENTS

| | | |
|---|---|---|
| EP | 1593337 A1 | 9/2005 |
| GB | 1513495 A | 6/1978 |

(Continued)

OTHER PUBLICATIONS

Japanese Office Action for Application Serial No. 2014-076939, mailed Oct. 6, 2015, pp. 1-2.

*Primary Examiner* — Timothy J Neal
(74) *Attorney, Agent, or Firm* — Tarolli, Sundheim, Covell & Tummino LLP

(57) ABSTRACT

A medical device sheath that includes a relatively inelastic body having a proximal end longitudinally separated from a distal end and defining a first lumen, an aperture located at the proximal end in fluid communication with the lumen and configured to admit an elongate endoscope body into the first lumen, and a transparent tip located longitudinally adjacent to an endoscope lens when the elongate endoscope body is located within the first lumen. The endoscope sheath may also include an elongate secondary tube defining a secondary lumen. A method of using the medical device sheath is also described.

3 Claims, 8 Drawing Sheets

(56) References Cited

U.S. PATENT DOCUMENTS

| | | | | |
|---|---|---|---|---|
| 5,863,287 | A * | 1/1999 | Segawa | A61B 1/00142 600/121 |
| 6,309,346 | B1 * | 10/2001 | Farhadi | A61B 1/00156 600/114 |
| 6,911,005 | B2 | 6/2005 | Ouchi et al. | |
| 7,815,565 | B2 * | 10/2010 | Stefanchik | A61B 1/00073 600/104 |
| 8,007,432 | B2 * | 8/2011 | Vakharia | A61B 1/00135 600/104 |
| 2002/0188280 | A1 | 12/2002 | Nguyen et al. | |
| 2003/0130564 | A1 | 7/2003 | Martone et al. | |
| 2003/0176769 | A1 | 9/2003 | Soble et al. | |
| 2006/0020165 | A1 * | 1/2006 | Adams | A61B 1/00094 600/121 |

FOREIGN PATENT DOCUMENTS

| | | |
|---|---|---|
| JP | 06134433 | 9/1996 |
| WO | 2008090540 A2 | 7/2008 |

* cited by examiner

MEDICAL DEVICE SHEATH

CROSS REFERENCE TO RELATED APPLICATIONS

This application is a continuation of U.S. patent application Ser. No. 13/257,529, filed Mar. 7, 2012, which claims priority under 35 U.S.C. §119(e) to U.S. Provisional Application Ser. No. 61/163,171, filed on Mar. 25, 2009, the entire disclosure of which is expressly incorporated herein by reference.

TECHNICAL FIELD

The present invention relates to an apparatus and method of use for a medical device sheath and, more particularly, to a medical device sheath which is suction-fitted to a medical device such as an endoscope.

BACKGROUND OF THE INVENTION

It is an axiom of medicine that medical devices invading or associating with a patient's body are required to be extremely clean, if not sterilized. This is particularly true with instruments, such as endoscopes and bronchoscopes, which pass through a body orifice, such as the urethra, anus, etc. Unless these instruments are sterilized between uses, the opportunities for passing disease-bearing organisms between patients are enhanced.

Sterilizing medical devices generally requires gas-sterilization. The process usually takes twenty-four hours and, as such, is not practical for instruments used several times a day. Instead, many instruments are soaked in a germicidal solution that is of questionable efficacy. The soaking takes at least ten minutes, which is advantageous over the gas sterilization process. However, the germicidal solutions tend to be caustic and will cause the premature destruction of the medical devices.

Several alternatives are contemplated to resolve this problem. The use of disposable instruments, such as disposable endoscopes, has been suggested. However, this would result in an unjustifiably high cost.

SUMMARY OF THE INVENTION

An alternative solution is the application of a sanitary disposable sheath for the medical devices. According to one aspect, a medical device sheath is embodied as an endoscope sheath. The endoscope sheath includes a relatively inelastic sheath body having a proximal sheath end longitudinally separated from a distal sheath end. The relatively inelastic sheath body defines a sheath lumen. The endoscope sheath also includes a scope aperture located at the proximal sheath end in fluid communication with the sheath lumen that is configured to admit an elongate endoscope body into the sheath lumen, and a sheath tip located at the distal sheath end. At least a portion of the sheath tip is configured to permit energy transmission therethrough and is located longitudinally adjacent to an endoscope lens when the elongate endoscope body is located within the sheath lumen. Examples of energy are visible light, infrared light, echo, and ultrasound. The endoscope sheath includes an evacuation fitting in fluid communication with the sheath lumen that is configured for selective removal of fluid from the sheath lumen. The endoscope sheath can also include an elongate secondary tube having a proximal secondary tube end longitudinally separated from a distal secondary tube end and defining a secondary lumen. At least a portion of the secondary lumen extends substantially parallel to the sheath lumen.

In some embodiments, the relatively inelastic sheath body will substantially maintain its thickness when positive or negative pressure is applied to it. In some embodiments, the evacuation fitting may include a valve having a pilot balloon coupled thereto. In some embodiments, the sheath body may be formed from a first material and the sheath tip may be formed from a second material. Additionally, in some embodiments, the first material may be polytetrafluoroethylene. In some embodiments, the second material may be silicone rubber. In some embodiments, the elongate secondary tube may be formed from the first material. When the sheath tip is formed from a second material, that second material can be more elastic than the first material.

Additionally, in some embodiments, a handle fitting may be positioned at the proximal sheath end. The handle fitting may be configured to create a fluidtight seal between elongate endoscope body and the endoscope sheath. In some embodiments, the elongate secondary tube may be secured to the relatively inelastic sheath body. In some embodiments, the distal secondary tube end may be positioned adjacent to the distal sheath end and may have an aperture in fluid communication with the secondary lumen.

In some embodiments, the secondary tube may be sized to receive a second medical device. In some embodiments, the endoscope sheath may include an elongate third tube having a proximal third tube end longitudinally separated from a distal third tube end and defining a third lumen. At least a portion of the third lumen may extend substantially parallel to the sheath lumen. In other embodiments, more tubes that are similar to the secondary tube can be added to the endoscope sheath. For example, the secondary tube can receive a medical device while a third tube can provide suction.

According to another aspect, a method of using an endoscope sheath is disclosed. The method includes inserting an endoscope body into a lumen of an elongate tubular body of the endoscope sheath, creating a fluidtight seal between the endoscope body and the elongate tubular body, and removing fluid from between the endoscope body and the elongate tubular body to bring the elongate tubular body into contact with the endoscope body. In some embodiments, the elongate tubular body of the endoscope sheath may be relatively inelastic.

In some embodiments, removing fluid from between the endoscope body and the elongate tubular body may include creating negative pressure within the lumen of the elongate tubular body. In some embodiments, inserting the endoscope body into the lumen of the elongate tubular body may include placing a distal end of the endoscope body in contact with the distal end of the elongate tubular body. Additionally, in some embodiments, the method may also include applying a lubricant or other material to one of the endoscope body and the elongate tubular body to reduce a coefficient of friction between the endoscope body and the elongate tubular body.

According to another aspect, the medical device sheath includes a relatively inelastic body having a proximal end longitudinally separated from a distal end. The relatively inelastic body defines a first lumen. The medical device sheath includes an aperture located at the proximal end in fluid communication with the first lumen that is configured to admit a medical device body into the first lumen, and a sheath tip located at the distal end. The sheath tip is configured to permit energy transmission therethrough and is located longitudinally adjacent to a medical device end when the medical device body is located within the first lumen. The medical device sheath also includes an elongate secondary tube defining a secondary lumen, and a plurality of apertures are defined at the distal end of the relatively inelastic body and at least one of the apertures in fluid communication with the secondary lumen of the elongate secondary tube.

In some embodiments, the medical device sheath may also include an evacuation fitting in fluid communication with the first lumen and configured for selective removal of fluid from the first lumen. In some embodiments, the evacuation fitting may include a valve having a pilot balloon coupled thereto. The pilot balloon can be configured to indicate when negative pressure is being maintained within the elongate tubular body. For example, the pilot balloon can indicate negative pressure by deflating. In some embodiments, the plurality of apertures may be arranged in a circular pattern.

BRIEF DESCRIPTION OF THE DRAWINGS

For a better understanding of the invention, reference may be made to the accompanying drawings, in which.

DETAILED DESCRIPTION OF THE DRAWINGS

Figure 1:
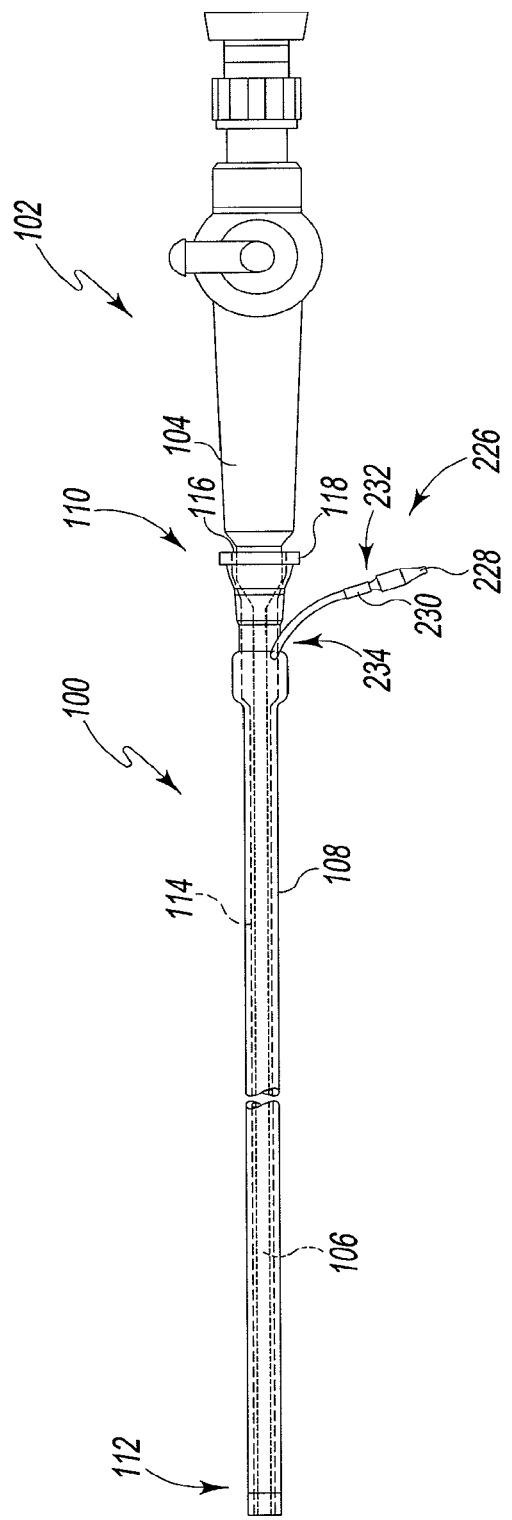
FIG. 1 is a side elevation view of one embodiment of a medical device sheath associated with an endoscope.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Referring now to FIG. 1, a medical device sheath is shown as endoscope sheath 100. The endoscope sheath 100 is shown in place on an endoscope 102 of a known type. The endoscope 102 has an endoscope handle 104 and an elongate endoscope body 106. The endoscope sheath 100 includes an elongate tubular sheath body 108 having a proximal sheath end 110 longitudinally separated from a distal sheath end 112. The sheath body 108 is formed from a relatively inelastic material. The term "relatively inelastic" as used herein refers to a material that will not perceptibly stretch longitudinally when an external force is applied. One example of a relatively inelastic material is polytetrafluoroethylene ("PTFE") that does not perceptibly stretch when an external force is applied. In some embodiments, the relatively inelastic sheath body may substantially maintain its thickness when positive or negative pressure is applied to it.

The sheath body 108 defines a sheath lumen 114 extending from the closed distal sheath end 112 to a scope aperture 116 located at the proximal sheath end 110. In that way, the scope aperture 116 is in fluid communication with the sheath lumen 114 and is configured to admit the endoscope body 106 into the sheath lumen 114. As shown in FIG. 1, the proximal sheath end 110 has a handle fitting 118 secured thereto. The handle fitting 118 is flared to extend over the tip of the endoscope handle 104. The handle fitting 118 is formed from silicone rubber and is configured to form a fluidtight seal between endoscope handle 104 and the endoscope sheath 100.

The sheath body 108 has a longitudinal dimension that covers the operative length of the endoscope body 106, which will be inserted into the patient, and extends beyond the operative length of the endoscope body 106 to prevent contamination of the endoscope 102. The sheath body 108 has an initial diameter sufficiently larger than that of the endoscope 102 such that the endoscope is allowed to slip into the endoscope sheath 100 with a low degree of friction therebetween, thereby avoiding damage to either the endoscope 102 or the endoscope sheath 100. It will be appreciated that a lubricant or other material to reduce the coefficient of friction may be separately provided or included in the material of the endoscope sheath 100 to facilitate sliding of the endoscope sheath 100 along the endoscope body 106.

Figure 2A:
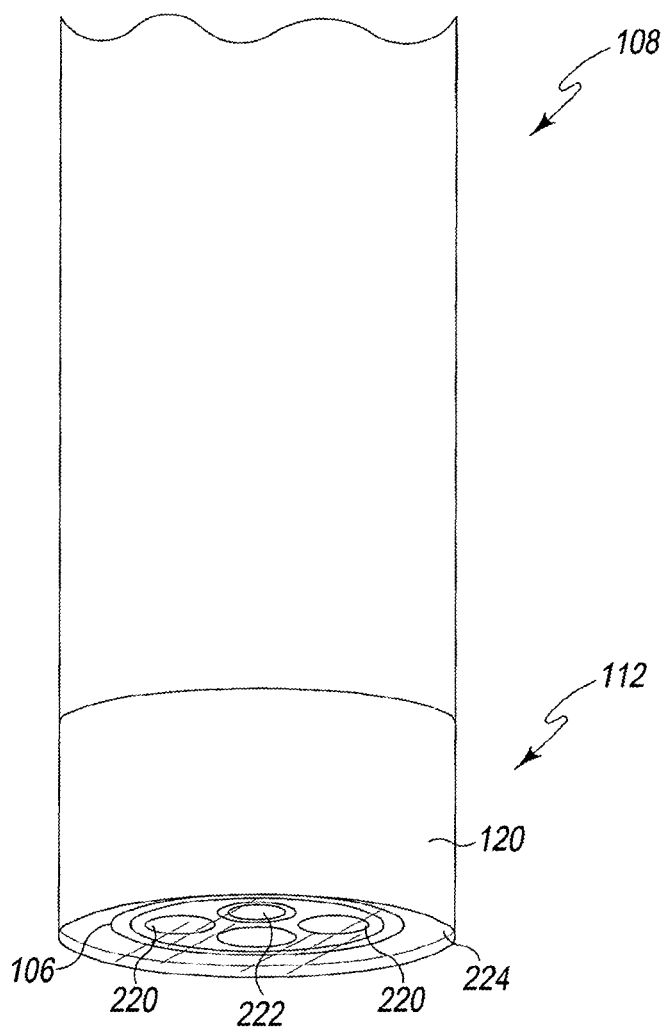
FIG. 2A is fragmentary perspective view of the embodiment of FIG. 1.
Figure 2B:
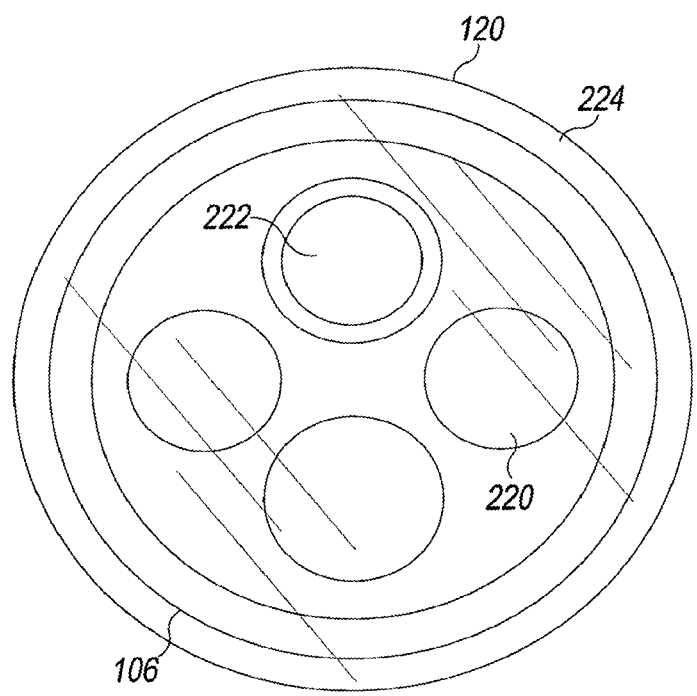
FIG. 2B is a bottom plan view of the embodiment of FIG. 1.

Referring now to FIGS. 2A and 2B, four example endoscope channels 220 are shown, which extend through the endoscope body 106 in a known manner. One of the endoscope channels 220 contains an endoscope lens 222, and one or more of endoscope channels 220 may contain another endoscope lens, a lighting source (not shown), or another surgical aid or accessory (not shown). Because the endoscope sheath 100 provides a fluidtight barrier between the endoscope 102 and the patient's body, any surgical tool or other manipulative/invasive device extending through the endoscope channel 220 for mechanical (i.e., not merely visual or other electromagnetic wave) interaction with the patient's body would not be appropriate for use with the illustrative embodiment of FIGS. 1-2B.

As shown in FIG. 2A, a sheath tip 120 is located at the distal sheath end 112. The sheath tip 120 extends coaxially with the sheath body 108 and operatively closes off the sheath lumen 114 at the distal sheath end 112. It will be appreciated that the sheath tip 120 may be of any suitable length and may be attached to the distal sheath end 112 in any suitable manner. The sheath tip 120 includes a laterally extending end portion 224 that is configured to permit energy transmission therethrough and is located longitudinally adjacent to the endoscope lens 222. Examples of such energy are visible light, infrared light, ultraviolet light, echo, and ultrasound. In that way, the sheath tip 120 can facilitate various functional modalities included in the endoscope 102, such as, for example, ultrasound and fiber optics contained within the endoscope channels 220. The endoscope 102 or other medical device positioned in the sheath lumen 114 may be the source and/or the receiver of the energy transmission.

In the illustrative embodiment of FIGS. 1-2B, the sheath tip 120 is formed from silicone rubber. The sheath tip 120 may also be formed from a thin, flexible, tissue- or film-like elastic material that is transparent and permits the sheath tip 120 to flex with the endoscope body 106. It will be appreciated that in other embodiments the sheath tip 120 may at least partially take the form of a hard lens or a solid disc made of a clear plastic material.

The sheath tip 120 and sheath body 108 may each be integrally formed or aggregated from separate components. As described above, the sheath body 108 is made from a first material, PTFE, while the sheath tip 120 is made from a second material, silicone rubber. In other embodiments, the sheath tip 120 and sheath body 108 may be made of the same material. For ease of use with the endoscope 102, at least a portion of the endoscope sheath 100 should be made of a thin, flexible, tissue- or film-like elastic material, which may be transparent.

When the endoscope body 106 is fully inserted into the sheath body 108, the end portion 224 of the sheath tip 120 is held in close proximity to, or in contact with, the endoscope lens 222 to facilitate energy transmission through the sheath tip 120. Contact between the endoscope lens 222 and the end portion 224 of the sheath tip 120 prevents undesirable reflections that might occur if the end portion 224 were spaced apart from the endoscope lens 222. To facilitate positioning between the end portion 224 and the endoscope lens 222, the end portion 224, the sheath tip 120, or any other suitable portion of the endoscope sheath 100 may be made of an elastic material or other appropriate material configured to bias the end portion 224 longitudinally toward the endoscope lens 222 tightly. In some embodiments, a soft transparent material may be applied between the endoscope lens 222 and the end portion 224. The soft transparent material may be, for example, transparent silicon gel. In some embodiments, a small gap may be formed between the endoscope lens 222 and the sheath tip 120.

Returning to FIG. 1, the endoscope sheath 100 includes an evacuation fitting 226 in fluid communication with the sheath lumen 114. The evacuation fitting 226 is positioned near the proximal sheath end 110. It will be appreciated that in other embodiments the evacuation fitting 226 may be located at any point on the sheath body 108. It will also be appreciated that the endoscope sheath 100 may include additional evacuation fittings.

The evacuation fitting 226 includes a valve 228 coupled to a hose 230 at an end 232. The hose 230 extends from the end 232 to an end 234 secured to a lateral side of the sheath body 108. The hose 230 has a lumen (not shown) extending therethrough that fluidly couples the sheath lumen 114 with the valve 228. When the valve 228 is open, the evacuation fitting 226 provides a fluid path between the ambient atmosphere and the sheath lumen 114.

The valve 228 of the evacuation fitting 226 is configured to regulate the selective removal of fluid (such as, but not limited to, air, saline, body fluids, oxygen, nitrogen, sterilizing fluid, and/or lubricant) from the sheath lumen 114. The valve 228 is operable to regulate the movement of fluid into and out of the hose 230. As shown in FIGS. 1-2B, the valve 228 is configured to accept a vacuum line from a negative pressure source and includes a pilot balloon to indicate whether negative pressure is being maintained in the sheath lumen 114. For example, the pilot balloon may deflate to indicate a negative pressure within the sheath lumen 114.

One example of an evacuation fitting 226 is a Mallinckrodt™ Intermediate Hi-Lo Tracheal Tubing, Cat. No. 86450, commercially available from Covidien of Mansfield, Mass. In other embodiments, the evacuation fitting 226 may include other valves or devices configured to accept a syringe, vacuum line, or other positive or negative pressure source, and may include a one-way valve to facilitate fluid passage therethrough in a desired direction. It is also contemplated that saline or another fluid could also be supplied to the sheath lumen 114 through the evacuation fitting 226. In order to facilitate fluid removal from the sheath lumen 114, the handle fitting 118 located at the proximal sheath end 110 prevents fluid from entering the endoscope sheath via the scope aperture 116 under suction pressure applied to the sheath lumen 114 through the evacuation fitting 226.

In use, the endoscope sheath 100 acts as a contaminant barrier for the endoscope 102. To position the endoscope sheath 100 on the endoscope 102, the user may, if desired, apply lubricant or other material to reduce the coefficient of friction to one of the endoscope and the endoscope sheath before inserting the endoscope body 106 into the sheath body 108 through the scope aperture 116. The endoscope sheath 100 is then drawn up along the endoscope body 106 (or the endoscope body is pushed further into the endoscope sheath) until the endoscope body has reached a desired position within the endoscope sheath. For example, the endoscope body 106 could be pushed into the endoscope sheath 100 until the endoscope lens 222, or another distal location on the endoscope body 106, comes into contact with an inner side of the sheath tip 120. Optionally, the handle fitting 118 at the proximal sheath end 110 may provide a "stop" or motion-limiting function to prevent further penetration of the endoscope body 106 into the sheath lumen 114.

Optionally, when the sheath tip 120 or related structures are elastic or otherwise adapted for a closely gripping fit to the endoscope body 106, the user can unroll (in a condom-like action) the sheath tip 120 onto the distal end of the endoscope or otherwise associate the sheath tip 120 snugly with the endoscope before the rest of the sheath body 108 is placed around the endoscope body 106.

Once the endoscope 102 has reached its desired position with respect to the sheath lumen 114, the initial diameter of the sheath body 108 is sized such that the sheath body 108 fits relatively loosely around the endoscope body 106. A vacuum line, syringe, or other source of negative pressure is then attached to the evacuation fitting 226 in a substantially fluidtight manner, and negative pressure is applied to the sheath lumen 114 through the evacuation fitting 226. With assistance of the handle fitting 118 or other sealing feature located at the proximal sheath end 110 (which could be as simple as an elastic band holding the distal sheath end tightly around the endoscope 102), the negative pressure source is used to suction-fit the flexible endoscope sheath 100 to the endoscope 102. As fluid is removed from between the endoscope 102 and the endoscope sheath 100, the initial diameter of the sheath body 108 contracts and the sheath body 108 is substantially brought into contact with the outside of the endoscope body 106, as shown in FIG. 1. This type of connection is sometimes called a "vacuum fit," though there need not be an actual vacuum formed between the two connected structures. The valve 228 is configured to prevent fluid from passing back into the sheath lumen 114 when the negative pressure source is removed. When the valve 228 includes a pilot balloon, the state of the pilot balloon indicates the pressure in the sheath lumen 114. Alternately or additionally, the material of the endoscope sheath 100 could be chosen to maintain the suction-fit connection.

This close fitting of the endoscope sheath 100 to the endoscope body 106 (and optionally to at least some portion of the endoscope handle 104) may provide a sterilized covering for the endoscope 100 that flexes and turns along with the endoscope during use. The close fitting also avoids the "binding up" of the installed endoscope sheath at bend areas of the endoscope. Additionally, in some embodiments, the transparency of all or part of the endoscope sheath 100 may assist a user with positioning and using the covered or sheathed endoscope 102.

Referring now to FIGS. 3-5B, other embodiments of a medical device sheath are illustrated. Some features of the embodiments illustrated in FIGS. 3-5B are substantially similar to those discussed above in reference to the embodiment of FIGS. 1-2B. Such features are designated in FIGS. 3-5B with the same reference numbers as those used in FIGS. 1-2B.

Figure 3:
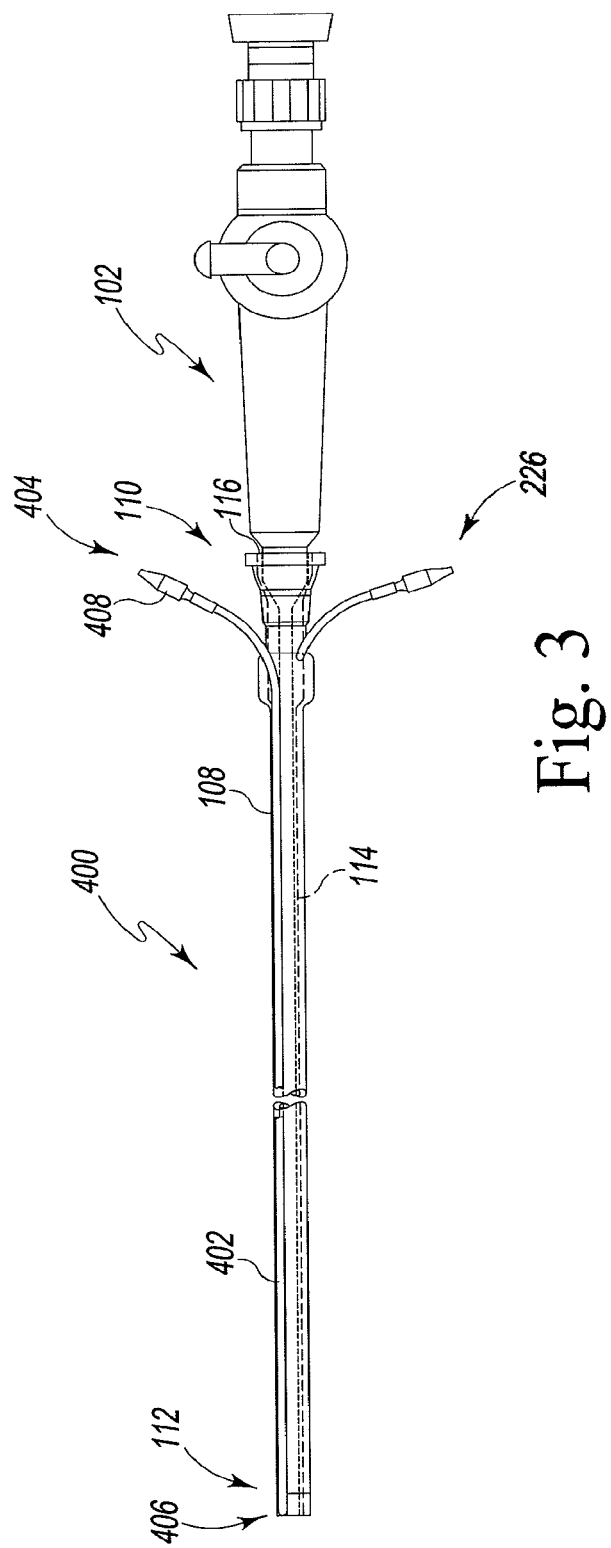
FIG. 3 is a side elevation view of another embodiment of a medical device sheath associated with an endoscope.

Referring to FIG. 3, in another embodiment, an endoscope sheath 400 is shown in place on the endoscope 102. Similar to the endoscope sheath of FIGS. 1-2B, the endoscope sheath 400 includes a sheath body 108 having a proximal sheath end 110 longitudinally separated from a distal sheath end 112. The sheath body 108 defines a sheath lumen 114 extending from a closed distal sheath end 112 to a scope aperture 116 located at the proximal sheath end 110. A sheath tip 120 is located at the distal sheath end 112.

The endoscope sheath 400 also includes an elongate secondary tube 402 secured to the sheath body 108. The secondary tube 402 has a proximal secondary tube end 404 longitudinally separated from a distal secondary tube end 406. The secondary tube 402 has a secondary lumen 410 (see FIG. 4A) extending substantially parallel to the sheath lumen 114 from a lower aperture 412. The secondary tube 402 also includes a secondary tube fitting 408 located at the proximal secondary tube end 404 to allow the user to access the secondary lumen 410 and the distal secondary tube end 406 from outside the patient's body. The secondary tube 402 may be integrally formed or constructed from component parts and may be made of any appropriate material or combination of materials. For example, the secondary tube 402 could be at least partially made of the same material as the sheath body 108, which, as discussed above, may be polytetrafluoroethylene ("PTFE").

Figure 4A:
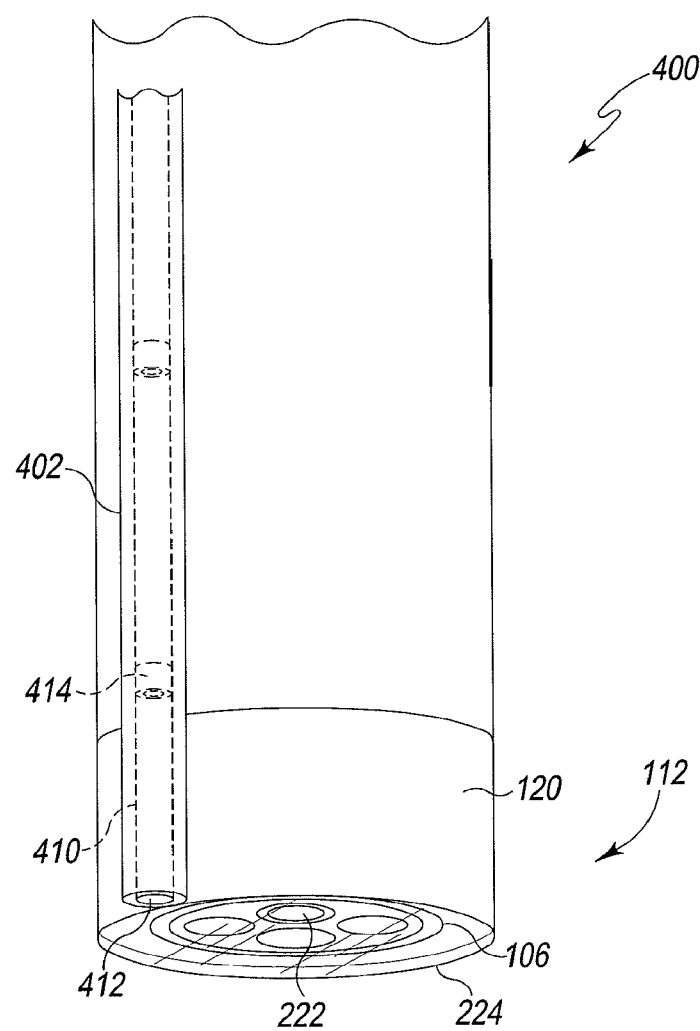
FIG. 4A is fragmentary perspective view of the embodiment of FIG. 3.
Figure 4B:
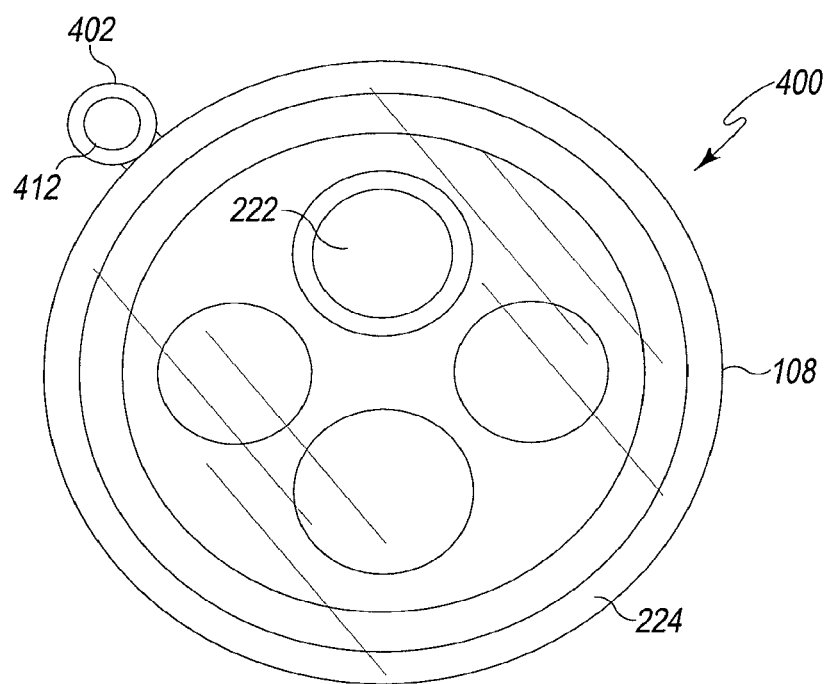
FIG. 4B is a bottom plan view of the embodiment of FIG. 3.

As shown in FIGS. 4A and 4B, a number of secondary support members 414 are positioned within the secondary lumen 410. The support members 414 provide additional support to the secondary lumen 410 such that the lumen 410 remains open when subjected to lateral pressure from other portions of the endoscope sheath 100 or neighboring structures of the patient's body (not shown). The secondary support members 414 are made of an at least semi-rigid material and include a longitudinally extending hole therethrough to prevent the secondary lumen 410 from pinching shut under lateral pressure. It will be appreciated that in other embodiments the number of support members 414 may be increased or decreased and may even be omitted.

In use, the user may advance saline or another fluid through the secondary tube 402 to the distal sheath end 112. In that way, an end portion 224 of the sheath tip 120 may be rinsed. A negative pressure source may also be coupled to the proximal secondary tube end 404 to suction away debris or undesirable fluids that might obscure the endoscope lens 222. Further, the secondary tube 402 could be used to provide access for additional medical devices such as cutters, cauterizers, forceps, balloon catheters, or other tools of any desired type to a surgical site within the patient's body.

It will be appreciated that in other embodiments the secondary tube 402 may be substantially located within the sheath lumen 114, depending upon whether the secondary tube 402 is intended to provide access/fluid communication to/from the patient's body or to/from the sheath lumen 114. A secondary tube tip (not shown) could be located at, and extend coaxially with, the distal secondary tube end 406, in a manner analogous to the previously described sheath tip 120 and distal sheath end 112 arrangement of the embodiment of FIGS. 1-2B. When present, the secondary tube tip could provide fluid communication between the secondary lumen 410 and an area adjacent the end portion 224 of the sheath body 108. The secondary tube tip could also be made of any appropriate material or combination of materials and attached to the distal secondary tube end 406 in any suitable manner. It will be appreciated that in other embodiments the endoscope sheath 400 may also include additional tubes similar to secondary tube 402. For example, in one embodiment, the endoscope sheath 400 may include an additional tube to provide suction while a medical device is inserted into the secondary tube 402. In that way, the endoscope sheath 400 would have both a suction tube and a working tube.

Figure 5A:
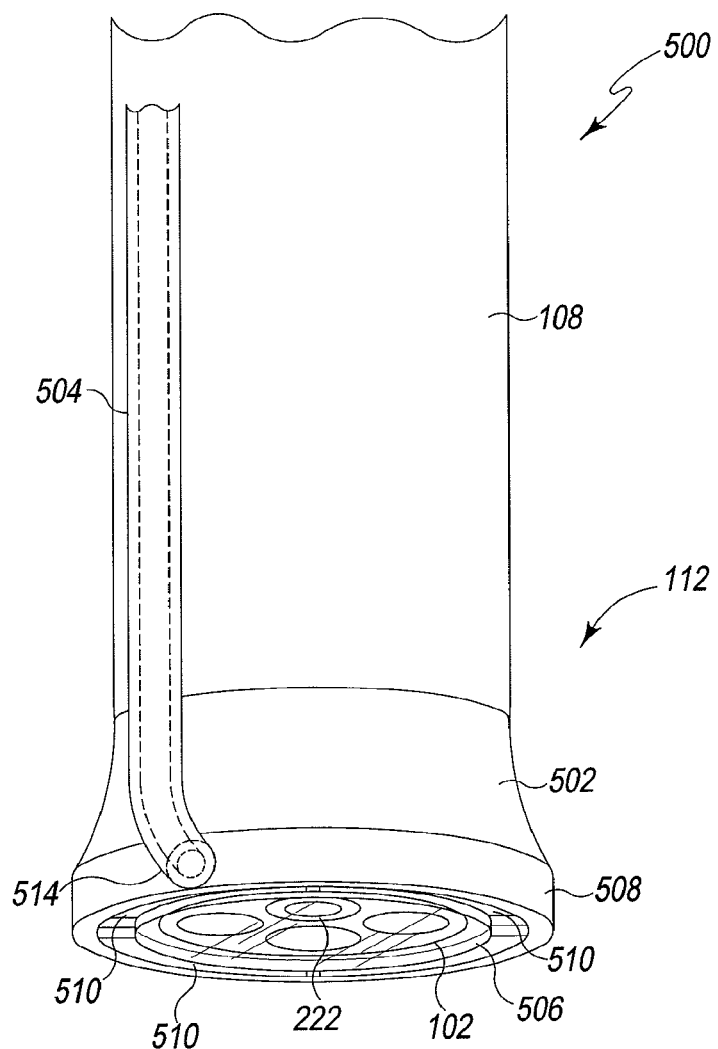
FIG. 5A is fragmentary perspective view of another embodiment of a medical device sheath.
Figure 5B:
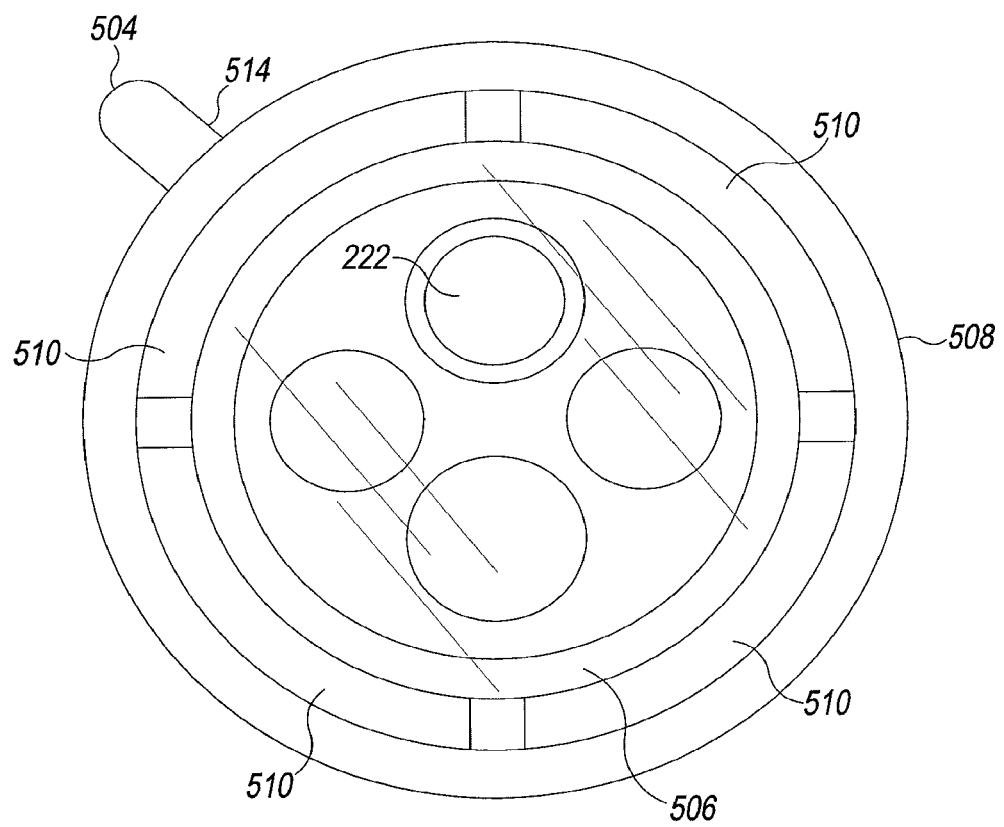
FIG. 5B is a bottom plan view of the embodiment of FIG. 5A.

Referring to FIGS. 5A and 5B, in another embodiment, an endoscope sheath 500 is shown. Similar to the endoscope sheath of FIGS. 1-4B, the endoscope sheath 500 includes a sheath body 108 having a proximal sheath end (not shown) longitudinally separated from a distal sheath end 112. The endoscope sheath 500 includes a sheath tip 502 that is located at the distal sheath end 112 and a secondary tube 504 secured to the sheath body 108.

The sheath tip 502, like the sheath tip of FIGS. 1-2B, extends coaxially with the sheath body 108 and operatively closes off a sheath lumen (not shown) of the sheath body 108 at the distal sheath end 112. The sheath tip 502 also includes a laterally extending end portion 506 that is configured to permit energy transmission therethrough and is located longitudinally adjacent to the endoscope lens 222 of endoscope 102.

A suction port housing 508 is also located at the distal sheath end 112. The housing 508 has a plurality of apertures 510 defined therein that are arranged in a circular pattern about the end portion 506 of the sheath tip 502 (see FIG. 5B). The housing 508 has a passageway (not shown) that fluidly couples each of the apertures 510 to a distal end 514 of the secondary tube 504. In other embodiments, the housing 508 may include additional apertures and the apertures may be arranged differently. It will also be appreciated that in other embodiments fewer apertures may be included.

The housing 508 may be integrally formed or constructed from component parts and may be made of any appropriate material or combination of materials. For example, the housing 508 could be at least partially made of the same material as the sheath body 108, which, as discussed above, may be polytetrafluoroethylene ("PTFE"). Alternatively, the housing 508 may also be made from the same material as the sheath tip 502, such as, for example, silicone rubber.

The secondary tube 504 extends from the distal end 514 to a proximal end (not shown). Similar to the embodiment of FIGS. 3-4B, a negative pressure source may also be coupled to the proximal end of the secondary tube 504. When a negative pressure source is coupled to the secondary tube 504, debris or undesirable fluids which might be obscuring the endoscope lens 222 may be drawn into the apertures 510 and into the passageway before being advanced along the length of secondary tube 504.

It will be appreciated that in other embodiments the endoscope sheath 500 may also include additional tubes similar to secondary tube 504. In some embodiments, not all of the apertures 510 may be in fluid communication with the secondary tube 504. For example, in one embodiment, the endoscope sheath 500 may include an additional tube to provide suction through one of the apertures 510 while a medical device is inserted into the secondary tube 504. In that way, the endoscope sheath 500 could also have both a suction tube and a working tube.

It will be understood by those of ordinary skill in the art that various additional embodiments may be contemplated without departing from the spirit and scope of the present disclosure. For example, one or more valve or seal structures (not shown) could be provided to allow a surgical tool or other manipulative/invasive device to extend through the sheath tip 120 and allow mechanical interaction between a tool inserted through an endoscope channel 220 and the patient's body while maintaining a substantially fluidtight barrier between the endoscope 102 and the patient's body. Saline could be provided to the sheath lumen 114 near an inner side of the end portion 224 through an endoscope channel 220, in order to rinse the endoscope lens 222 within the sheath lumen, with the used saline being removed from the sheath lumen through the evacuation fitting 226. The evacuation fitting 226 could remove fluid from the sheath lumen 114 at and/or near the point at which the evacuation fitting pierces the sheath body 108, or an evacuation tube (not shown) of any suitable type (which may be perforated) could extend in any direction and to any length within the sheath lumen to convey fluid to the evacuation fitting for removal from the sheath lumen.

It will also be appreciated that a medical device sheath similar to the endoscope sheath described above may be used with medical devices other than an endoscope. For example, another embodiment of the medical device sheath may be used with transesophageal echocardiogram transducer or bronchoscope. Similarly, another embodiment of the medical device sheath may be used with the fiberscope or other rigid airway medical device. The medical devices positioned in the sheath lumen may be the source and/or the receiver of the energy transmission.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

What is claimed is:

1. A medical device sheath comprising:
   a relatively inelastic body, the relatively inelastic body having a proximal end longitudinally separated from a distal sheath end and defining a first lumen,
   an aperture located at the proximal end in fluid communication with the first lumen and configured to admit a medical device body into the first lumen,
   a sheath tip located at the distal end, the sheath tip being configured to permit energy transmission therethrough and being located longitudinally adjacent to a medical device end when the medical device body is located within the first lumen, the sheath tip extending coaxially with the sheath body and operatively closing off the sheath lumen,
   an elongate secondary tube defining a secondary lumen, the elongate secondary tube being secured to an outer surface of the sheath body;
   an evacuation fitting in fluid communication with the sheath lumen and configured for selective removal of fluid from the sheath lumen such that the sheath body contracts and is substantially brought into contact with an outside of the medical device, the evacuation fitting including a valve having a pilot balloon that is coupled thereto and in fluid communication with the sheath lumen, the pilot balloon being configured to indicate the pressure in the sheath lumen, and
   a suction port housing located at the distal sheath end, the suction port housing having a plurality of apertures defined therein that are arranged in a pattern about an end portion of the sheath tip, the suction port housing having a passageway that fluidly couples each of the apertures to the secondary lumen of the secondary tube.

2. The medical device sheath of claim 1, wherein the plurality of apertures are arranged in a circular pattern.

3. An endoscope sheath consisting of:
   a relatively inelastic sheath body, the relatively inelastic sheath body having a proximal sheath end longitudinally separated from a distal sheath end and defining a sheath lumen;
   a scope aperture located at the proximal sheath end in fluid communication with the sheath lumen and configured to admit an elongate endoscope body into the sheath lumen;
   an elongate secondary tube defining a secondary lumen, the elongate secondary tube being secured to an outer surface of the sheath body;
   a secondary tube fitting located at a proximal secondary tube end;
   at least one secondary support member disposed within the secondary lumen of the secondary tube;
   wherein the distal secondary tube end is positioned adjacent the distal sheath end and has an aperture in fluid communication with the secondary lumen;
   a sheath tip located at the distal sheath end, at least a portion of the sheath tip being configured to permit energy transmission therethrough and being located longitudinally adjacent to an endoscope lens when the elongate endoscope body is located within the sheath lumen, the sheath tip extending coaxially with the sheath body and operatively closing off the sheath lumen; and
   an evacuation fitting in fluid communication with the sheath lumen and configured for selective removal of fluid from the sheath lumen such that the sheath body contracts and is substantially brought into contact with an outside of the endoscope body, the evacuation fitting including a valve having a pilot balloon that is coupled thereto and in fluid communication with the sheath lumen, the pilot balloon being configured to indicate the pressure in the sheath lumen.

* * * * *